United States Patent
Prins et al.

(10) Patent No.: US 10,620,195 B2
(45) Date of Patent: Apr. 14, 2020

(54) DYNAMIC SWITCHING BIOSENSOR

(71) Applicant: Technische Universiteit Eindhoven, Eindhoven (NL)

(72) Inventors: Menno Willem José Prins, Rosmalen (NL); Peter Zijlstra, Utrecht (NL); Lucas Brunsveld, Nuenen (NL)

(73) Assignee: Technische Universiteit Eindhoven, Eindhoven (NL)

( * ) Notice: Subject to any disclaimer, the term of this patent is extended or adjusted under 35 U.S.C. 154(b) by 142 days.

(21) Appl. No.: 15/526,019

(22) PCT Filed: Nov. 12, 2015

(86) PCT No.: PCT/EP2015/076423
§ 371 (c)(1),
(2) Date: May 11, 2017

(87) PCT Pub. No.: WO2016/075229
PCT Pub. Date: May 19, 2016

(65) Prior Publication Data
US 2017/0315115 A1    Nov. 2, 2017

Related U.S. Application Data

(60) Provisional application No. 62/159,235, filed on May 9, 2015, provisional application No. 62/132,096, filed
(Continued)

(51) Int. Cl.
*G01N 33/543* (2006.01)
*C12Q 1/68* (2018.01)
(Continued)

(52) U.S. Cl.
CPC ..... *G01N 33/54306* (2013.01); *C12Q 1/6816* (2013.01); *C12Q 1/6825* (2013.01);
(Continued)

(58) Field of Classification Search
CPC ................ C12Q 1/6816; C12Q 1/6825; C12Q 2565/107; C12Q 2565/133;
(Continued)

(56) References Cited

U.S. PATENT DOCUMENTS

| | | | |
|---|---|---|---|
| 8,405,379 B1 * | 3/2013 | Montagnier | G01N 37/005 324/76.12 |
| 2003/0003510 A1 * | 1/2003 | Bray | C12Q 1/66 435/7.1 |

(Continued)

FOREIGN PATENT DOCUMENTS

| | | |
|---|---|---|
| WO | WO2007070542 | 6/2007 |
| WO | WO2008020823 | 2/2008 |
| WO | WO2015067302 | 5/2015 |

OTHER PUBLICATIONS

Schena et al. Modulating protein activity using tethered ligans with mutually exclusive binding sites. Nature Communications 2015 vol. 6(22) p. 7830. Published online Jul. 22, 2015. doi: 10.1038/ncomms8830.

(Continued)

Primary Examiner — Maureen Wallenhorst
(74) Attorney, Agent, or Firm — Lumen Patent Firm

(57) ABSTRACT

An analyte in a matrix is sensed using a sensing device having a detection probe conjugated to a mediator-receptor that is not a binder for the analyte. The sensor device is provided with mediators conjugated to analyte-receptors, where the mediators are selected to bind to the mediator-receptors, and where the analyte-receptors are selected to bind to the analyte. In some embodiments, the mediators are bound to the detection probe by a tether molecule, or tether molecule fragment, or tether domain. In other embodiments, the mediators are not bound to the detection probe. The presence of the analyte is detected by optically or electrically detecting changes of distance between the mediators (Continued)

and the mediator-receptor, indicative of association and/or dissociation events between mediators and mediator-receptor, the characteristics of which are affected by whether the analyte is bound to the analyte-receptor.

6 Claims, 7 Drawing Sheets

Related U.S. Application Data on Mar. 12, 2015, provisional application No. 62/092,763, filed on Dec. 16, 2014, provisional application No. 62/078,870, filed on Nov. 12, 2014.

(51) Int. Cl.
*G01N 33/542* (2006.01)
*G01N 33/68* (2006.01)
*C12Q 1/6816* (2018.01)
*C12Q 1/6825* (2018.01)

(52) U.S. Cl.
CPC ..... *G01N 33/542* (2013.01); *G01N 33/54313* (2013.01); *G01N 33/54373* (2013.01); *G01N 33/6872* (2013.01)

(58) Field of Classification Search
CPC ........ C12Q 2565/607; C12Q 2565/628; G01N 33/542; G01N 33/54306; G01N 33/54313; G01N 33/54373; G01N 33/6872
USPC ............. 436/63, 149, 164, 501; 435/7.1, 7.8
See application file for complete search history.

(56) References Cited

U.S. PATENT DOCUMENTS

2003/0108972 A1* 6/2003 Zweig .................. G01N 33/542
435/7.92
2017/0328894 A1* 11/2017 Zijlstra ................ G01N 33/542

OTHER PUBLICATIONS

Baaske et al. Single-molecule nucleic acid interactions monitored on a label-free microcavity biosensor platform. Nature Nanotechnology 9, 933-939 (2014) doi:10.1038/nnano.2014.180.

Cao et al., "Gold nanoparticle-based signal amplification for biosensing" Analytical Biochemistry 417 (2011) 1-16.

Parab et al., "A gold nanorod-based optical DNA biosensor for the diagnosis of pathogens" Biosensors and Bioelectronics 26 (2010) 667-673.

Abel et al., "Fiber-Optic Evanescent Wave Biosensor for the Detection of Oligonucleotides" Anal. Chem. 1996, 68, 2905-2912.

Wadle et al., "Mediator probe PCR: detection of real-time PCR by label-free probes and a universal fluorogenic reporter." Methods Mol Biol. 2014;1160:55-73.

Faltin et al., "Mediator probe PCR: a novel approach for detection of real-time PCR based on label-free primary probes and standardized secondary universal fluorogenic reporters." Clin Chem. Nov. 2012;58 (11):1546-56.

Li et al. "Electrogenerated chemiluminescence aptasensor for ultrasensitive detection of thrombin incorporating an auxiliary probe." Talanta. Dec. 2014;130:370-6.

* cited by examiner

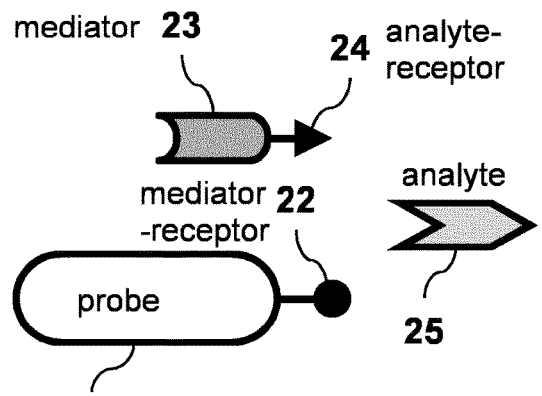
*Fig. 2A*
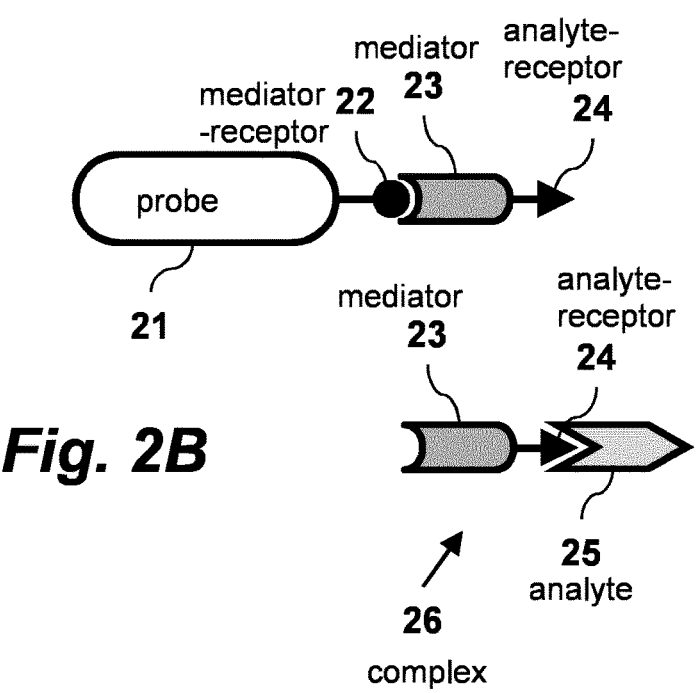
*Fig. 2B*
*Fig. 2C*
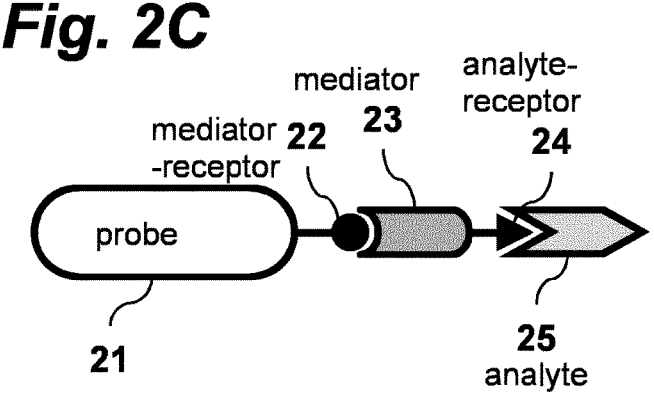

Fig. 3A
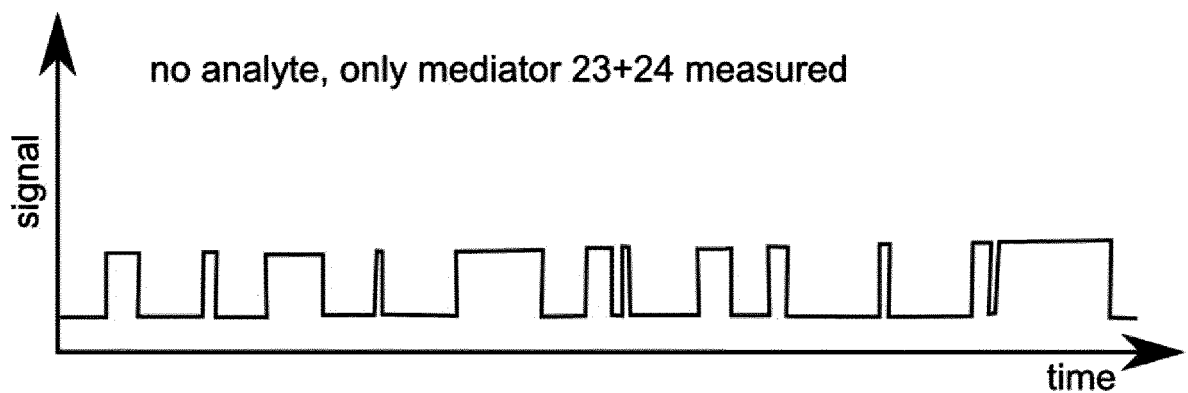
no analyte, only mediator 23+24 measured
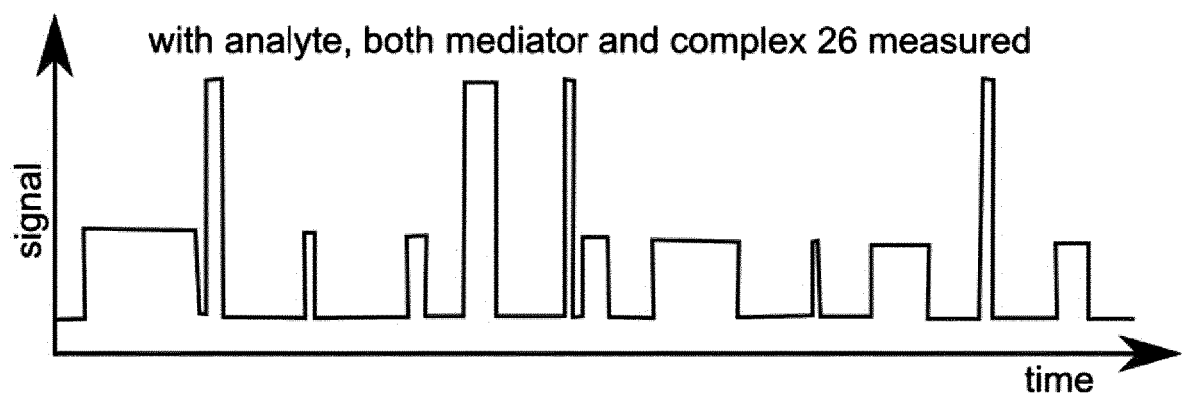
with analyte, both mediator and complex 26 measured
Fig. 3B

DYNAMIC SWITCHING BIOSENSOR

CROSS-REFERENCE TO RELATED APPLICATIONS

This application is a 371 of PCT application PCT/EP2015/076423 filed on Nov. 12, 2015. PCT/EP2015/076423 filed on Nov. 12, 2015 claims the benefit of U.S. Provisional Applications 62/159,235 filed on May 9, 2015, 62/132,096 filed on Mar. 12, 2015, 62/092,763 filed on Dec. 16, 2014, and 62/078,870 filed on Nov. 12, 2014.

FIELD OF THE INVENTION

The present invention relates generally to biochemical detection and monitoring. More particularly, the invention relates to a biosensing device for the detection of analyte in fluid.

BACKGROUND OF THE INVENTION

In-vivo monitoring is typically done using electrochemical sensors, but those are only suited for high-concentration analytes, e.g., glucose. It remains a problem to detect low-concentration analytes with high specificity in a complex biological matrix (or a derivative thereof), e.g., in blood plasma, whole blood, skin interstitial fluid, gland fluid, tear fluid, mucus, mucous glands, saliva, cells, etc.

A recent development is biosensors based on single-molecule detection principles, where the binding of an analyte molecule to a probe results in a detection signal with a digital characteristic, e.g., an analyte molecule is present or is not-present. Single-molecule detection has distinct advantages over ensemble-averaged techniques because it yields statistical distributions of molecular properties instead of averages and reveals rare and unsynchronized events. An example of such a biosensor with analyte-receptor is illustrated is FIGS. 1A-B. Biosensing probe 11 carries at least one analyte-receptor 12 on its surface. Biosensing probe 11 can be a molecular or a supramolecular moiety, a particle, a surface, a pore, a tip, etc. Attached to the probe 11 is an analyte-receptor 12 which is selected to bind to analyte 13. FIG. 1A shows the probe configurations with a free analyte 13 and FIG. 1B shows the probe configuration with a bound analyte 13. The transition from unbound to bound states is characterized by an on-rate $k_{on}$, while the transition from bound to unbound states is characterized by an off-rate $k_{off}$.

One problem of the biosensor in FIGS. 1A-B is that analytes are typically detected by using recognition molecules with strong binding affinities, such as, e.g., antibody-like molecules. These molecules bind strongly and therefore have low off-rates (low $k_{off}$). A problem is that low off-rates result in extended blocking times because the bound analyte occupies the receptor. This will not only limit the statistics that can be gathered in a certain time-frame, but will also result in a slow response time of the sensor, which is problematic for real-time monitoring applications.

Another problem with the biosensor in FIGS. 1A-B is accuracy. A biosensor system should be accurately known in order to avoid misinterpretation of the measured signals, e.g., baseline characteristics (e.g., drift), noise, sensitivity, signal-to-noise ratio. A difficulty is that signal and noise characteristics can change over time, e.g., due to variations in an optical excitation system (e.g., incident power), variations in an optical detection system (e.g., focal drift), variations in a probe property (e.g., due to temperature changes), variations in molecular properties on a probe (e.g., number of active molecules on the probe, mobility of signalling molecules on the probe surface), or variations of a property of the sample fluid (e.g., viscosity). These variations are easily misinterpreted as being signals, which reduces the accuracy and reliability of the sensor.

Another problem is that detection of different analytes requires the use of different recognition molecules on the particle, and therefore the development of novel procedures to couple recognition molecules to the probe.

SUMMARY OF THE INVENTION

To address the shortcomings of existing approaches, embodiments of the invention provide a biosensor with a molecular architecture that gives both high specificity and still highly dynamic signals with high off-rates, which improves statistics and sensor response time. Embodiments of the invention also provide a biosensor with a molecular architecture that allows real-time calibration of a biosensor already prior to binding of an analyte molecule. This improves the reliability of the biosensing system. In addition, embodiments of the invention provide a biosensor with a modular architecture that is suited for different analytes.

In one aspect, embodiments of the present invention provide a biosensor using a mediator to overcome slow off-rates of the analyte from the analyte-receptor. The detector probe binds to the mediator probe with fast off-rates, while the mediator probe selectively binds to the target analyte.

In another aspect, embodiments of the present invention provide a biosensing system with a mediator-receptor bound to a probe, a mediator selected to bind to the mediator-receptor, and an analyte-receptor bound to the mediator, where the analyte-receptor is selected to bind to the target analyte. In some embodiments, the mediator may be bound to the probe by a tether, while it other embodiments it is not bound to the probe.

In a non-tethered system, the at least one mediator-receptor and the at least one mediator are in the environment of each other, but they are not tethered to each other, so they have a large motional freedom and can move away from each other, e.g., due to thermal diffusion. In a system with a plurality of mediator moieties in the environment of a given mediator-receptor, the given mediator-receptor can interact with the several mediator moieties due to their large motional freedom. The system is dynamic due to the motion of at least one of the moieties and due to the occurrence of a plurality of interaction events over time.

In a tethered system, at least one mediator-receptor (or probe) and at least one mediator are tethered to each other, so they have a limited range of motional freedom with respect to each other. Due to the tether, the at least one mediator-receptor and the at least one mediator are maintained in proximity, with a maximum separation distance determined by the maximum length of the tether. Due to excitation of the moieties, e.g., due to thermal motion, the system is dynamic and the at least one mediator-receptor interacts in repetition with the at least one mediator.

A special property of the biosensor is that the dynamic binding and unbinding of the mediator to the mediator-receptor on the biosensing probe gives a time-dependent signal that depends on the presence and/or binding and/or concentration of analyte.

A method for sensing an analyte according to embodiments of the invention include bringing a matrix (e.g., a fluid or analyte-permeable matrix) containing the analyte into contact with a sensor device having a detection probe conjugated to a mediator-receptor that is not a binder for the analyte. The sensor device is provided with mediators conjugated to analyte-receptors, where the mediators are selected to bind to the mediator-receptors, and where the analyte-receptors are selected to bind to the analyte. In some embodiments, the mediators are bound to the detection probe by a tether molecule, or tether molecule fragment, or tether domain. In other embodiments, the mediators are not bound to the detection probe. The method also includes detecting by an optical or electrical sensor changes of distance and/or relative orientation between the mediators and the mediator-receptor, indicative of association and/or dissociation events between mediators and mediator-receptor. A characteristic of association and/or dissociation events depends on whether the analyte is bound to the analyte-receptor. The presence of the analyte is determined by a processor from the detected changes of distance between mediator and mediator-receptor while the matrix is in contact with the sensor device, which may include performing histogram and/or histogram processing to suppress background noise and enhance specificity.

In some embodiments, the detection probe is a particle with free charge carriers with a plasmon resonance that changes with the distance and/or relative orientation between the mediator and the mediator-receptor. Detecting changes of distance and/or relative orientation between the mediators and the mediator-receptor may then include exciting free charge carriers in the detection probe particle (e.g., by exposing the detection probe to optical or electrical energy, such as with a superluminescent diode), and detecting optical radiation from the detection probe particle. The exciting and/or detection is performed using a wavelength near the plasmon resonance wavelength of the detection probe particle while the matrix containing the analyte is in contact with the sensor device.

In other embodiments, the detection probe may be a pore of which the ionic conductivity changes with the distance between the mediator and the mediator-receptor. Detecting changes of distance between the mediators and the mediator-receptor may then include applying a voltage difference over or ionic current through the pore while the matrix containing the analyte is in contact with the sensor device, and detecting the current through or voltage difference over the pore.

BRIEF DESCRIPTION OF THE DRAWINGS

FIGS. 2A-C illustrate various configurations of a biosensing technique using a non-tethered mediator, according to an embodiment of the invention.

FIGS. 3A-B are graphs of a detection signal as a function of time, where signal levels indicate different binding configurations, according to embodiments of the invention.

DETAILED DESCRIPTION

Figure 1A:
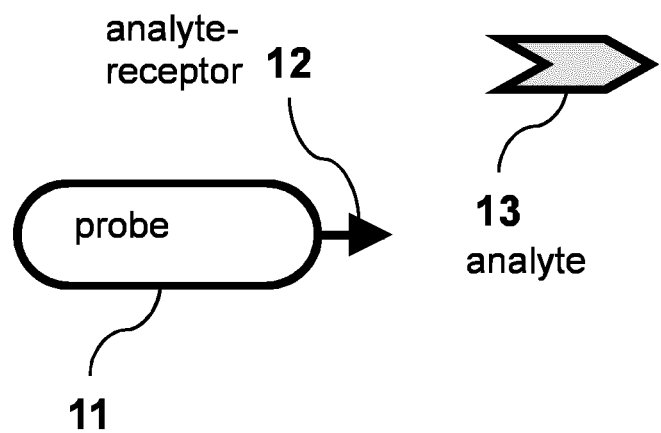
FIGS. 1A-B illustrate two configurations of a single-molecule detection technique using an analyte-receptor, as known in the art.
Figure 1B:
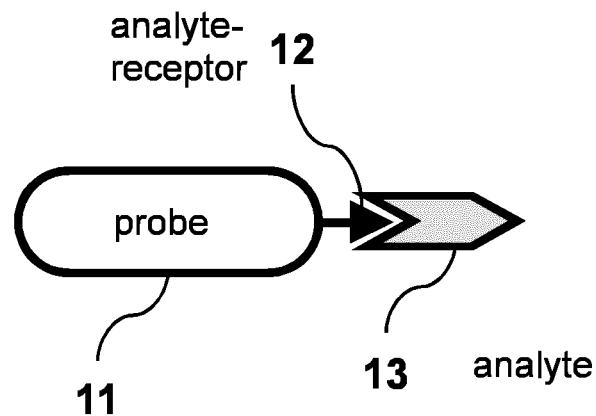

A biosensing technique using a non-tethered mediator according to one embodiment of the invention is schematically illustrated in FIGS. 2A-C.

As shown in FIG. 2A, biosensing probe 21 carries at least one mediator-receptor 22 on its surface. Mediator 23 is conjugated to at least one analyte-receptor 24, and is present in the environment of at least one probe 21. This configuration represents a probe 21 with a mediator-receptor 22 to which no mediator 23 is bound, and a mediator 23 to which no analyte 25 is bound. As shown in FIG. 2B, mediator 23 can bind to mediator-receptor 22. Alternatively mediator 23 can also bind to analyte 25 via analyte-receptor 24, forming complex 26. As shown in FIG. 2C, Mediator 23 can simultaneously bind both to mediator receptor 22 and to analyte 25.

The probe 21 is a biosensing element that can report binding events with single-object resolution, where the object is a molecule, a macromolecule, a nanoparticle, etc. The probe can be a molecular or a supra-molecular moiety, a particle, a surface, a pore, a tip, etc. The physical sensing principle can be optical (e.g., spectroscopic, absorption, fluorescence), electrical (e.g., current), or mechanical (e.g., vibration property). In some embodiments, at least one probe is optically interrogated, e.g., a spectral property is detected (e.g., plasmonic detection) or a coordinate property is detected (e.g., particle motion and/or orientation of a label particle with respect to another object). In other embodiments, the mediator is conjugated to a signal-amplifying moiety (e.g., a gold nanoparticle or a fluorescent group, in order to enhance the amplitude of the signal due to mediator dynamics). In other embodiments, the analyte is provided (directly or indirectly) with a signal-amplifying moiety (for labelled detection, e.g., using a gold nanoparticle or a fluorescent particle, in order to enhance the amplitude of the signal when the analyte is bound).

In one implementation, the probe 21 can be a gold plasmonic nanorod, attached to a substrate, which could be an organic material (e.g., a polymer) or inorganic material (e.g., glass). The association and dissociation of biomolecules is measured with single-molecule resolution, e.g., via spectral shifts of the plasmon resonance. In other embodiments, the probe is a particle with a maximum diameter between 2 nanometer and 10 micrometer, or a cavity, or a nanopore, a tip or protrusion. The probe may be fabricated or attached to a surface or substrate of a flow cell.

In other embodiments, at least one probe is immobilized on a surface, mobile in solution or in a viscoelastic medium, embedded in a biological tissue or a cell, and/or embedded in a permeable matrix such as a gel or a porous matrix.

The probe can be functionalized with specific receptors, e.g., a receptor for mediator moieties. For example, a gold plasmonic nanorod can be provided with a mediator-receptor 22, e.g., a Ni-NTA moiety, with NTA equal to nitrilotriacetic acid, e.g., provided with a linker and a thiol group for coupling to the gold.

In solution, analyte molecules are present, which are of value to detect and/or quantify. The analyte can be e.g., a medical biomarker for health or disease. In a non-limiting example, the analyte can be C-reactive protein (CRP), a marker for inflammation. In other embodiments, the analyte may be at least one of the following, or a combination thereof: protein, peptide, nucleic acid, small molecule, metabolite, hormone, drug, enzyme, saccharide, carbohydrate, lipid, steroid, macromolecule, nanoparticle, virus, microorganism, or cell fragment.

The mediator-receptor (e.g., Ni-NTA) is preferably selected for not being a specific binder for the analyte (e.g., CRP). Rather, the mediator-receptor is preferably selected to bind specifically to a mediator moiety, which in this example is a His-tag. The analyte (e.g., CRP) does not bind directly with the mediator-receptor moiety (e.g., Ni-NTA) on the probe (e.g., gold nanorod). For binding to the probe, mediator-coupled analyte receptor (e.g., His-tagged anti-CRP capture molecules, e.g., His-tagged Fab fragments) are used, which function as mediator/analyte-receptor molecules 23, 24.

In some embodiments, the analyte-receptor may be conjugated or incorporated in close proximity of or in partial overlap with the binding region of either the mediator or the mediator-receptor, so that binding of analyte to the analyte-receptor significantly hinders or modifies the binding between mediator and mediator-receptor. Thus, analyte binding modulates or hinders mediator/mediator-receptor binding and thereby changes the association or dissociation process between mediator and mediator-receptor.

In the absence of analyte, the mediator 23 will dynamically interact (i.e., bind and unbind) with the mediator-receptor 22 on the probe 21. Due to the dynamic binding/unbinding and the high sensitivity of the probe, the probe generates a digital-like signal indicating the binding or unbinding, and/or presence or absence, of mediator moiety on the probe. An example of a signal as a function of time is shown in FIG. 3A, where every switch from low level to high level indicates a binding event, and a switch from high to low indicates an unbinding event. These two sensed signal levels correspond to the configurations shown in FIGS. 2A and 2B (disregarding the formation of the complex 26). More generally, a characteristic of the probe signal depends on whether an analyte molecule is bound to an analyte-receptor. For example, an analyte-induced change of probe signal characteristic relates to a signal magnitude characteristic and/or a time characteristic, such as a difference in amplitude of signal or in on-off times.

Significantly, this technique provides dynamic binding and unbinding events that can be detected at the single-molecule level, even in the absence of analyte, which provides a real-time control and/or calibration signal. For example, information present in the shape and statistics of the signal can be used to conclude whether or not the probe and the molecular sensing system are functioning properly. As another example, drift and noise can be suppressed, by filtering e.g., signal amplitude and/or in the time and/or in the frequency domain. As another example, the amplitude of the signal modulation allows calibration of the sensitivity of the probing system, e.g., the signal change per unit bound species. More generally, probe signal characteristics related to mediator dynamics (i.e., mediator/mediator-receptor association and/or dissociation) are recorded in a state when analyte is not bound to a mediator-conjugated analyte-receptor. These characteristics may then be used as a control and/or to calibrate the biosensing system.

When analyte is present in solution, the configuration shown in FIG. 2C is also sensed. As a result, the probe 21 reports signals from binding/unbinding of mediators 23 and/or binding/unbinding of mediator-analyte complexes 26. The mixed occurrence of these signals is indicated in FIG. 3B. The events cause different signals, in part because a mediator-analyte complex 26 is larger, so gives a higher signal modulation, than a mediator without analyte molecule. So the signal contains information about the binding/unbinding of both species.

The frequency of binding of mediators 23 is an indication of the concentration of free mediator in the environment of the probe. The frequency of binding of mediator-analyte complex 26 indicates the concentration of mediator-analyte complex in the environment of the probe. This gives the opportunity to perform signal processing, e.g., relate the mediator concentration to the mediator-analyte-complex concentration. If the total mediator-concentration is known, then the data can be used to quantify the concentration of analyte in the original sample.

Note that the timescale on which these interactions take place can be controlled, e.g., by the concentration and affinity of the mediator for the mediator-receptor. In some embodiments, the dissociation rate between mediator and mediator-receptor is higher than the dissociation rate between analyte and analyte-receptor, thereby improving statistics. In other embodiments, the dissociation rate between mediator and mediator-receptor is tuned by molecular modification of one molecular element thereof, or of the tether.

In this embodiment, the mediator concentration can be selected to achieve optimal biosensor performance properties. The use of a mediator concentration that is higher than the analyte concentration can give effective coupling of mediator to analyte, i.e., a large fraction of analyte molecules can become bound to a mediator moiety. The use of a mediator concentration higher than the $K_d$ (the equilibrium dissociation constant) of the analyte-receptor/analyte system (i.e., related to binding between 24 and 25), can give effective and rapid binding of mediator molecules to analyte molecules, i.e., a high fraction of analyte molecules can become bound to a mediator moiety, even for low analyte concentrations. The use of a mediator concentration that is close to the $K_d$ of the mediator/mediator-receptor system can give a high fractional occupancy of the mediator-receptor by mediator moiety. A high fractional occupancy combined with a high dissociation rate constant ($k_{off}$), gives frequent binding and unbinding between mediator and probe (dynamic equilibrium). In the example of FIGS. 3A-B, this results in frequent high-low and low-high transitions, so a signal with good transition statistics and a good response time.

The molecular nature of the mediator-receptor/mediator system allows for simple tuning of its binding characteristics such as $K_d$ and $k_{off}$, by engineering small chemical or biochemical changes in either the mediator-receptor and/or the mediator. Many possible changes are known in the field of chemical biology, protein engineering and molecular biology. In the above-mentioned example of a Ni-NTA/His-tag binding couple, examples of changes are, e.g., the valency of the NTA moiety, or the number of histidines. The molecular tuning allows optimizing the mediator-receptor/mediator interaction for the total biosensing system, which has more degrees of freedom than the analyte-receptor/analyte interaction. For example, the system can be designed to become less sensitive to the strength of the analyte/analyte-receptor interaction, which gives enhanced robustness.

Another advantage of the molecular biosensor architecture is that the surface chemistry on the probe can be identical for different analytes, because only the analyte-receptor coupled to the mediator needs to be adapted. The proposed system thus provides a modular and versatile approach for the detection of different analytes.

A similar embodiment is shown in FIGS. 4A-D, which is the same in principle as the embodiment of FIGS. 2A-C, except that the mediator is tethered to the probe rather than free in solution. As with the embodiment of FIGS. 2A-C, a probe 31 is bound to a mediator-receptor 32, and a mediator 33 is bound to an analyte-receptor 35. The mediator 33 is selected to bind to mediator-receptor 32, and the analyte-receptor is selected to bind to analyte 36. The mediator 33 in this embodiment of FIGS. 4A-D, however, is not free is solution but is bound to probe 31 by tether 34.

Figure 4A:
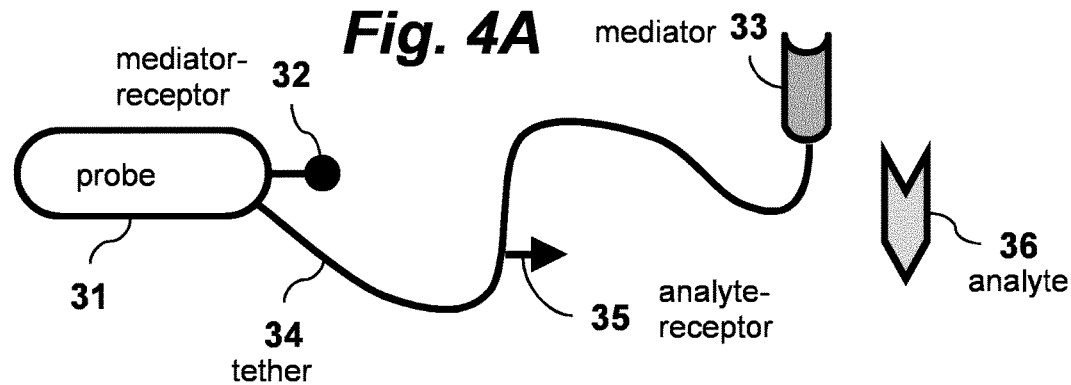
FIGS. 4A-D illustrate various configurations of a biosensing technique using a tethered mediator, according to an embodiment of the invention.
Figure 4B:
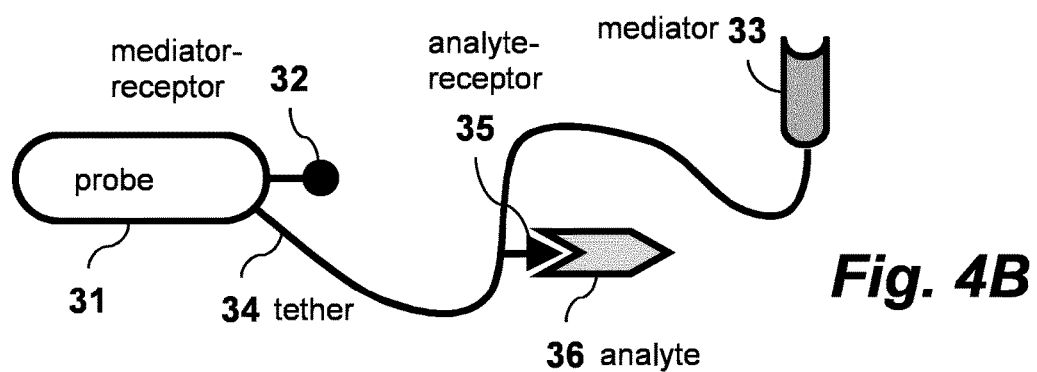
Figure 4C:
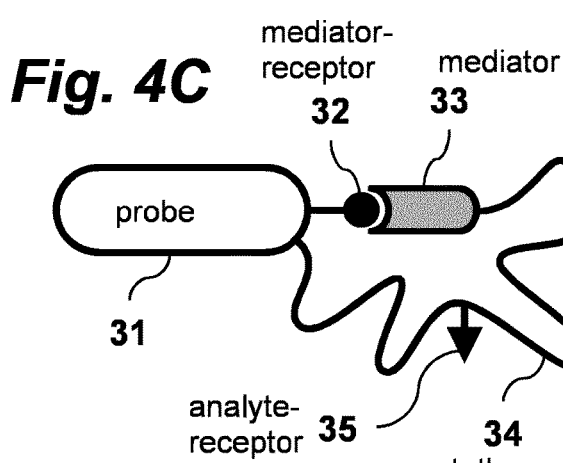
Figure 4D:
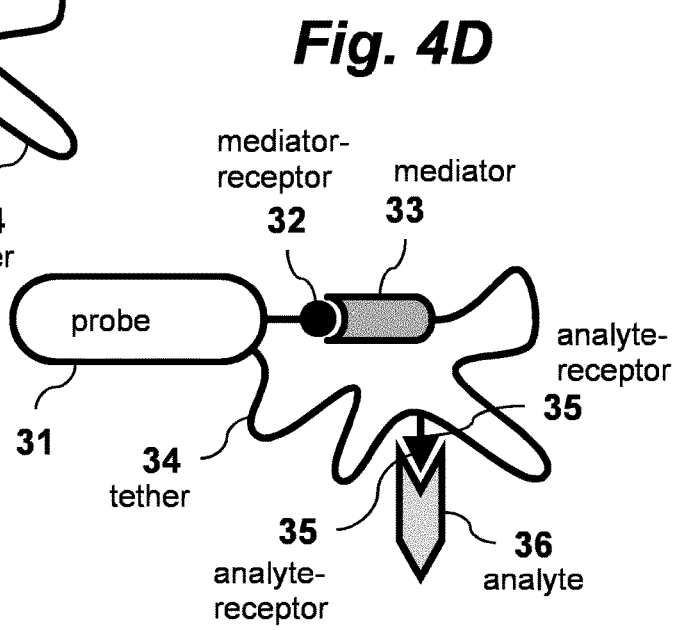

FIG. 4A shows a configuration where mediator 33 is not bound to the probe 31, and the analyte 36 is not bound to the analyte-receptor 35. FIG. 4B shows a similar configuration except that the analyte 36 is bound to the analyte-receptor 35. FIG. 4C shows a configuration where mediator 33 is bound to the probe 31 by mediator-receptor 32, and the analyte 36 is not bound to the analyte-receptor 35. FIG. 4A shows a similar configuration except that the analyte 36 is bound to the analyte-receptor 35. Switching between the two configurations of FIG. 4A and FIG. 4C give a signal like that of FIG. 3A, while switching between the two configurations of FIG. 4B and FIG. 4D give a signal like that of FIG. 3B.

The tether 34 can be a polymer, a biopolymer, a synthetic polymer, a peptide, a polypeptide, an oligonucleotide, an oligomer, an oligoamide, a protein, a nucleic acid, a single-stranded DNA, a double-stranded DNA, a PNA, oligo ethylene glycol, alkyl, or a combination thereof. This embodiment with tether can be advantageous when the reporting moiety needs to be very compact, or when it is preferred that a mediator interacts with a well-defined mediator-receptor and/or probe rather than with many mediator-receptors and/or probes, or when a high interaction rate is desired between mediator and mediator-receptor (e.g., by high local effective concentrations), or when long distance mediator travel or mediator leakage is not allowed (e.g., because it gives an uncontrolled process, or it represents an uncontrolled process or a safety risk, as may be the case in certain in-vivo applications).

The tethered design features the same molecular tuning properties as mentioned for the non-tethered design. In addition, the tethered design allows tuning of the chemical and biophysical nature of the tether, in order to tune the characteristics of the mediator-receptor/mediator system and/or make it sensitive to the binding of analyte to analyte receptor. E.g., tether length, tether flexibility (e.g., the bending persistence length), tether charge, modular build-up of the tether, etc., provide entries in modulating the mediator-receptor/mediator properties, e.g., the (un)binding dynamics, relative orientation and/or effective $K_d$. Thus the tether can be designed for optimal mediator-receptor/mediator interaction, and bring properties in optimal relation to e.g., the detection system or to the analyte-receptor/analyte binding kinetics. The analyte-receptor can be incorporated in the molecular construct in various ways. The binding of analyte can modulate the tether properties (e.g. stiffness, effective length, charge) and thereby affect the mediator/mediator-receptor association and/or dissociation processes. Analyte may bind on or near the tether with avidity, multivalency, or at multiple locations in sequence or at the same time, thereby changing the mediator/mediator-receptor association and/or dissociation processes, e.g., kinetics and/or equilibrium distribution. Alternatively or additionally, the analyte-receptor may be conjugated or incorporated in close proximity of or in partial overlap with the binding region of either the mediator or the mediator-receptor, so that binding of analyte to the analyte-receptor significantly hinders or modifies the association and/or dissociation processes between mediator and mediator-receptor.

Note that the system is modular, because a single mediator-receptor/mediator pair system can be used for detection of several analytes.

For simplicity of illustration, the embodiments above focus on the operation of a single detection probe with a single mediator-receptor, single mediator conjugated to single analyte-receptor for detecting single association and/or dissociation events between a mediator and a mediator-receptor. However, embodiments of the invention preferably have hundreds or thousands of detection probes, and each detection probe may have multiple mediator-receptors, possibly of distinct types. Corresponding mediators, of possibly distinct types, with analyte-receptors of possibly distinct types then can sense analytes of possibly distinct types. Such a sensor with a multitude of biosensor probes thus allows for parallel detection of the same and/or multiple analytes. It preferably contains at least 100 biosensor probes, or at least 1000 probes.

The mediator and mediator-receptor may be any of various appropriate molecules. For example, they may be Ni-NTA, His-tag, glutathione, glutathione S-transferase, SH2 peptide, SH2 domain, SH3 peptide, SH3 domain, peptide, 14-3-3 protein, protein peptide binding domain, peptide aptamer, nucleic-acid, peptide nucleic-acid, nucleic acid aptamer, strep-tag, biotin, desthiobiotin, SBP-tag, streptavidin, streptactin, avidin, synthetic host-guest systems, maltose, maltose binding protein, S-tag, Ribonuclease S, receptor-ligand systems. Preferably, the mediator/mediator-receptor couple has a bio-orthogonal character in the sample matrix of interest, so that a biological sample will give minimal interference in the reference signal. It will be advantageous if the mediator can be site-selectively and with well-defined valency incorporated in or near the analyte receptor.

In other embodiments, a mediator/mediator-receptor couple is an analyte-receptor/analyte-analogue couple, as may be implemented in a competitive assay format, suited for small-molecule analytes. In other embodiments, at least one mediator is provided as a reagent in the vicinity of the probe, either untethered, or conjugated to the at least one probe by a flexible tether.

Biosensing systems according to the present invention can be used for in-vitro applications, or for in-vivo applications, or very generally for testing of the human body. It may be used as part of a medical device such as a catheter, a patch, a tube, a needle, a fiber, a clip, a wire. It may be used to support medical treatment, or as part of a device for monitoring in or on the body. It can be used in a disposable format such as a cartridge, a tube, a titer plate.

In in-vivo applications, the probes may be in interaction with the biological system via a filter module (e.g., a coating that passes analyte of interest and hinders passage of other components) and/or via a material that ensures biocompatibility and good operation while in contact with the live system.

Embodiments may include various additional features, including various forms of multiplexing, e.g., analyte multiplexing, spatial multiplexing, spectroscopic multiplexing, probe functionality multiplexing. Embodiments may include parallelization of probes, for statistics or for dynamic range (e.g., different probe functionalizations, multiplexed in position and/or in optical property). Embodiments may include various probe coatings, probe coverages, various ways and materials to embed and locate the probe in a matrix, analyte separation components, cell separation components, for specificity and/or sensitivity, which is particularly important in complex biological systems. Embodiments may include an analyzer or readout instrument, which sends excitation into the sensor (e.g., optical, electrical, acoustic) and/or receives signals from the sensor and performs signal processing. The analyzer may also be used to transmit signals to other instruments and/or to a remote communication, processing and/or storage systems.

In one specific embodiment, a plasmonic biosensor is based on hundreds of individual gold nanorods with single-molecule sensitivity that are simultaneously monitored in real-time within a dark-field microscopy setup. The technique allows for the statistical analysis of single-molecule interactions without requiring any labeling of the analyte. The ability to probe hundreds of nanoparticles simultaneously provides a sensor with a dynamic range of 7 decades in concentration and enables the study of heterogeneity in molecular interactions. The biosensor is part of a biosensing system that overcomes limitations in the prior art by monitoring hundreds of single-molecule plasmonic sensors in real-time using total-internal-reflection excitation in a standard microscope.

In a specific implementation, the sensor is made of individual gold nanorods (average size 10 nm×40 nm) that were spin-coated on a coverslip. As described in more detail below in relation to FIGS. 6A-B, the sample is irradiated with a narrow-band light source in a prism-type total-internal reflection microscope, and the scattered intensity of the particles was projected onto a CCD camera. In this background-free imaging geometry, plasmon shifts induce changes in the scattering cross section at the illumination wavelength, causing variations in the detected scattered intensity.

Upon irradiation with light, the free conduction electrons of metallic nanostructures oscillate collectively, known as surface plasmon, because of its interaction with the light's electric field, with a resonant frequency that depends on the nanoparticles' size, shape, and composition. When the resonance conditions are met, the incident photon resonates with the surface plasmon, which leads to the absorbance and scattering of the incident light. Resonance and, hence, the wavelength of absorption depends on the nature of the metal, size of the nanostructure, its aspect ratio and the local dielectric environment around the nanostructure, which can be summed as the refractive index of the surrounding medium. For example, 13-nm gold nanoparticles show one absorption band in water at 520 nm. Other metallic nanostructures such as gold and silver nanorods and other shapes show two peaks, one peak due to resonance between lateral modes with light and one for resonance due to the longitudinal modes that is tunable from the visible through the near infrared, depending on the nanorod aspect ratio.

Like surface plasmon resonance (SPR), localized surface plasmon resonance (LSPR) can measure the changes in the local refractive index, which results in the concomitant shift in the wavelength peak in the extinction spectra. Unlike SPR, LSPR has a higher sensitivity to refractive index changes very close to the surface, within a range of 5-15 nm from the nanostructure surface, compared with approximately 200-300 nm from metal film surface in SPR. In both cases, the sensitivity decreases exponentially from the surface. Thus, the sensitivity of a LSPR biosensor can be increased by using a small bioreceptor near the surface.

In contrast to approaches based on organic fluorophores, the brightness of the scattered signal using plasmon resonance detection allows analog detection (in contrast to photon counting) and continuous microsecond integration times with high signal-to-noise ratios (S/N). Plasmon shifts may be measured by detecting the scattered signal using a fast silicon photodiode. To achieve a strong scattering signal against a low background, one embodiment of the invention uses total-internal-reflection excitation using a laser source. A shift of the plasmon resonance induces a subsequent change in the scattered intensity (typically a 20% signal change is observed for a 5 nm shift when the laser wavelength is on the wing of the plasmon). This allows detection of 5 nm plasmon shifts in 1 µs with S/N more than 10 for nanorods with an aspect ratio of 3 and a width greater than 25 nm. These integration times allows clear resolving of the transition path of single aptamers on timescales of 10-100 µs.

The timescales not only depend on the optical properties of the plasmonic particles but also on the hydrodynamic drag of the tethered gold sphere, in embodiments using a label particle conjugated to the mediator. Based on its diffusion coefficient, however, a 12.5 nm diameter gold sphere is estimated to take about 3 µs to move over a distance of 10 nm (the typical length-scale of the conformational change). This timescale is shorter than the transition path time and will therefore not significantly perturb the measurement.

The microsecond time-resolution of this plasmonic measurement technique allows one to directly resolve the transition between states. Importantly, the photostability of the plasmon resonance uniquely allows one to perform statistics on subsequent events on the same molecule.

Figure 5:
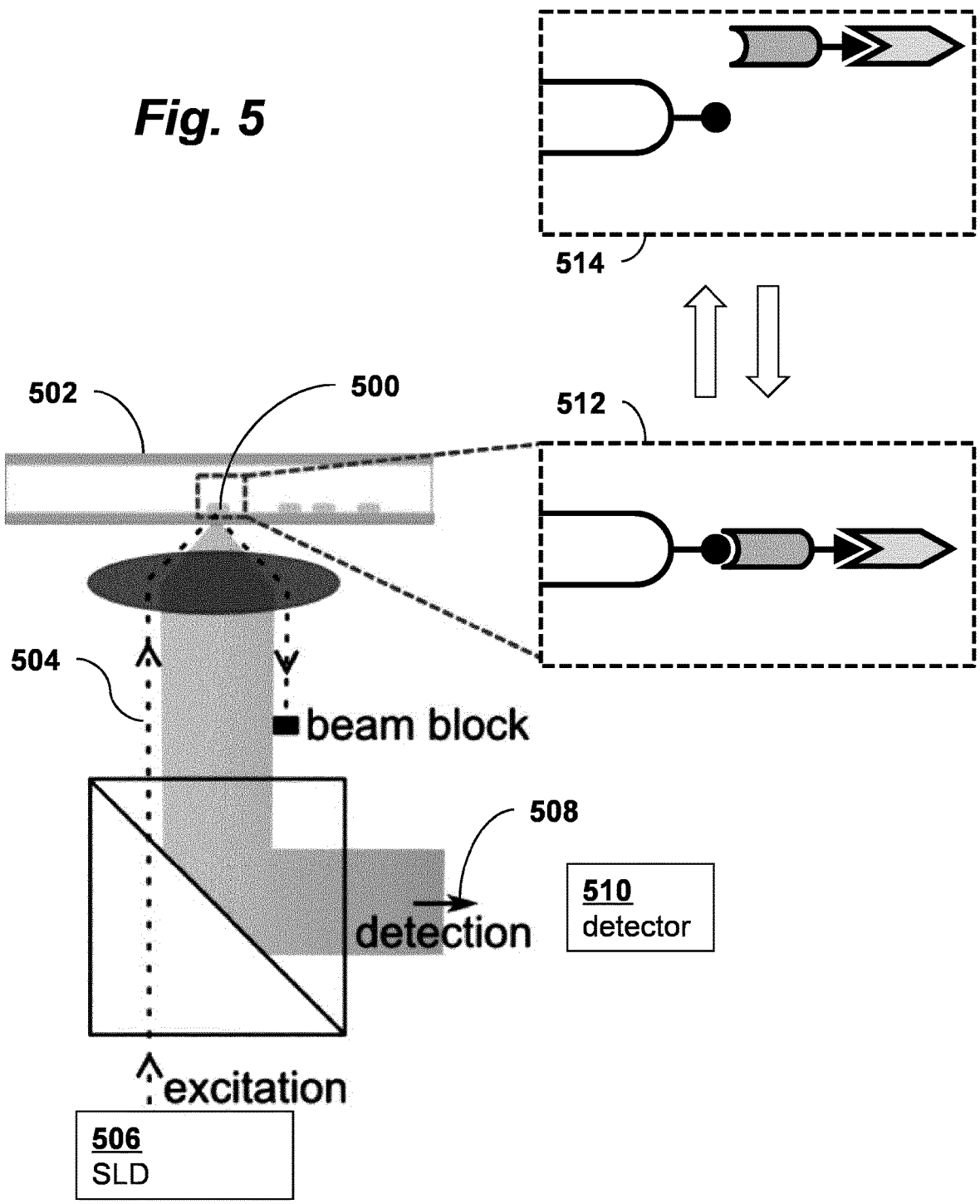
FIG. 5 is a schematic diagram illustrating an apparatus for implementing a biosensing technique using optical excitation and detection of plasmon resonance shifts according to an embodiment of the present invention.

FIG. 5 is a schematic diagram illustrating a technique for optical excitation and detection of plasmon resonance shifts in a sensor device according to an embodiment of the present invention. The nanorods 500 are immobilized onto coverslips in a flow-cell 502. An illumination beam 504 from a light source 112 preferably having a linewidth larger than 5 nm (e.g., superluminescent diode) undergoes total-internal-reflection in the wall of cell 502 and excites plasmons in the nanorod. An optical scattering signal 508 is directed to an optical detector 510, where it appears against a dark background, ensuring a high signal-to-noise ratio. Plasmon shifts between bound and unbound configurations 512 and 514 will then result in changes of detected signal intensity.

The detector 510 may be an electron multiplying charge-coupled-device (EM-CCD) which can image many individual dimers simultaneously. Alternatively, to reach microsecond integration times, the scattered intensity may be projected onto an analog photodiode.

Embodiments of the present invention may use techniques of dark field scattering spectroscopy. Specifically, it may use techniques using a bright low-coherence light source with a linewidth larger than 5 nm (e.g., a superluminescent diode) for dynamically measuring changes in the plasmon resonance peak of plasmonic particles.

Most detection methods for scattering objects such as metallic nanoparticles use dark-field illumination to obtain an image in which the object has a higher intensity than the background. For small particles (<100 nm in diameter for gold) the scattering signal reduces as the sixth power of the radius and quickly becomes swamped by the background. Imaging smaller objects therefore requires a high irradiance to obtain enough signal.

Imaging and/or spectroscopy of scattering objects is usually performed with a non-coherent white-light source (emission bandwidth >1000 nm). It allows for the imaging of scattering objects against a homogeneous and low background, and it can be used to extract a broadband scattering spectrum by determining the scattering signal at many different wavelengths using the same illuminator. Commonly employed sources are incandescent lamps (e.g., halogen) or arc-discharge sources (e.g., Xenon). The main disadvantage of these sources is their extended emitting area (>1 mm$^2$), which does not permit tight focusing of the beam to achieve a high irradiance of the sample.

One way to overcome this is by using a narrowband and coherent light source such as a laser. The high coherence and low bandwidth (typically <1 nm) allow for the tight focusing of the beam to achieve a high irradiance of the sample. However, coherent laser irradiation has limitations because (1) interference fringes cause an inhomogeneous illumination pattern and (2) small spurious reflections and leakage of light in the optical setup cause background artefacts in the image. Such artefacts significantly reduce the signal-to-noise ratio and may fluctuate in time due to vibrations and thermal drifts of the optical setup.

In such biosensing applications white-light sources or lasers are known to be useful to measure spectral shifts. White-light sources exhibit a spectral breadth B much larger than the line width Γ of a nanoparticle (i.e., B>>Γ), and thus allows for the measurement of the whole spectrum at once using a spectrometer. Shifts of the spectrum are then extracted by analyzing subsequent spectra. On the other hand, spectral shifts are also measured using a source that is much narrower than the line width of the particle, e.g., a laser (B<<Γ). The time-dependent scattered signal will change when the spectrum of the object shifts. However, because superluminescent diodes (SLDs) exhibit a spectral breadth that is similar to the line width of nanoparticles (i.e., B~Γ), the use of SLDs for dynamic spectral shift measurements on nanoparticles is unexpected.

Optical coherence tomography also uses SLDs for illumination, but there is no intention to measure spectral changes of the sample. Although particles with different plasmon resonances are used, the resonance wavelength is fixed and does not change in time. Thus, the measurement of dynamic behavior of plasmons using an SLD is unexpected because it is not intuitive to choose for a light-source that has a bandwidth only slightly narrower than the line width of the resonance that is probed.

The line width of a metal nanoparticle is typically 40-50 nm. A white-light source such as a halogen lamp has a line width much broader than a nanoparticle. A laser has a line width much narrower than a nanoparticle, whereas the line width of a typical SLD is typically 15-30 nm, depending on the emission wavelength, which is comparable to the line width of a nanoparticle.

Figure 6A:
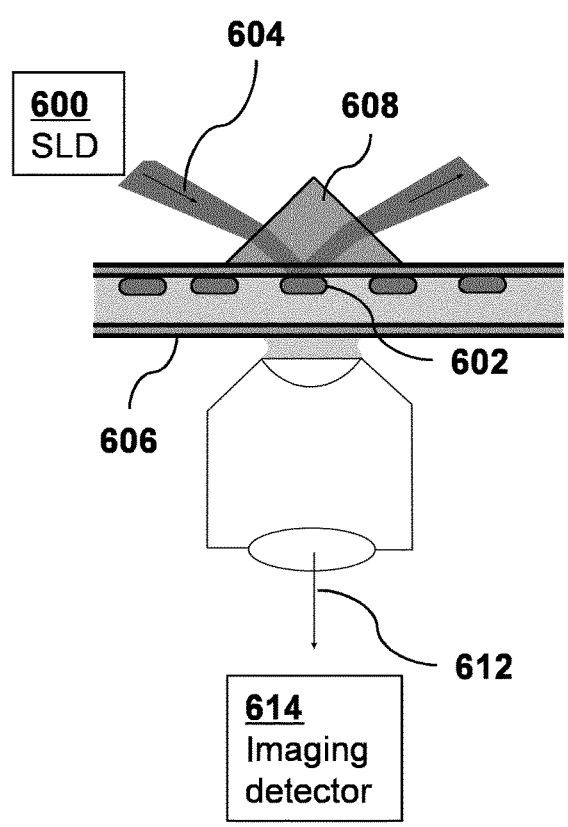
FIGS. 6A-B illustrate two implementations of a combined microscopy and spectroscopy method for biosensing using a superluminescent diode, according to an embodiment of the invention.
Figure 6B:
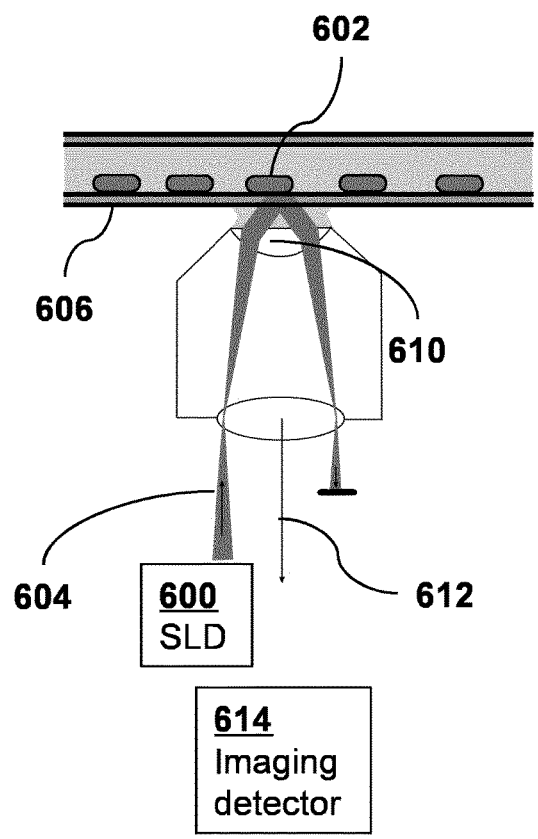

FIGS. 6A-B illustrate two implementations of a combined microscopy and spectroscopy method that use a bright and low-coherence light source, a superluminescent diode (SLD) 600, for the time-dependent imaging of scattering objects 602. In the biosensing techniques of embodiments of the present invention, the time-dependent signal represents shifts of the plasmon resonance peak of the scattering object indicative of the presence of an analyte. The shorter coherence length of the SLD light 604 compared to laser light significantly reduces the artefacts caused by interference, while the brightness of SLDs is similar to common diode lasers.

The low coherence and intermediate bandwidth (e.g., 15-30 nm at near-infrared wavelengths) of the beam result in homogeneous illumination and low background intensity. The high brightness and small emitting area (e.g., <30 μm$^2$ when coupled to a single-mode fiber) ensure a high irradiance. The scattering signal from an object illuminated with a superluminescent diode is high compared to the background and stable on short as well as long timescales.

In FIG. 6A the SLD 600 illuminates the sample 602 under an angle exceeding the angle for total internal reflection at a glass-water interface of a liquid cell 606. In this implementation, the light 604 is coupled to the sample 602 via a glass prism 608. In an alternate implementation, shown in FIG. 6B, the light 604 is coupled to the sample 602 via the back aperture of an objective lens 610. Because the implementation in FIG. 6A separates the excitation and emission light-paths, it leads to a lower background and higher signal-to-noise ratio than the implementation in FIG. 6B. The implementation in FIG. 6B may be useful if the space above the sample is to be used for other purposes, e.g., a technical component for temperature regulation. In both implementations, because the angle of illumination is higher than the angle for total-internal-reflection at the glass-water interface of the cell 606, all the excitation light is reflected. The presence of the particle 602 perturbs the total-internal-reflection, leading to a certain intensity of scattered light 612 that is partly collected by the objective and sent to an imaging sensor 614. The reflected beam is blocked by a beam-block, and the remaining scattered light is sent to an imaging detector, preferably a camera with sufficient dynamic range and wavelength sensitivity to achieve single-molecule resolution. In another embodiment, the sample 602 can be mounted on an optical probe (e.g., optical fibre) to allow for measurements to be conducted directly in complex biological environments.

The assay may involve e.g., a binding assay, a competitive assay, a displacement assay, a sandwich assay, an enzymatic assay, an assay with target and/or signal amplification, a multi-step assay, an assay with molecular cascade, etc. The assay may involve recognition moieties of different natures, e.g., peptides, proteins, nucleic acids, carbohydrates, etc. Embodiments may include various calibration methods, controls, multiplexing, etc. Embodiments may include measures to block and reduce unwanted processes (e.g., non-specific processes that generate background signals) and to increase efficiency, stability, and selectivity of signal generation.

Embodiments of the present invention include a system and technique for biosensing an analyte in a matrix using a large collection of nanoscale detectors whose optical properties are individually altered in the presence of an analyte. In preferred embodiments, for example, a plasmonic biosensor based on hundreds of individual gold nanorods with single-molecule sensitivity are simultaneously monitored in real-time within a dark-field microscopy setup.

We present a plasmonic biosensor based on hundreds of individual gold nanorods with single-molecule sensitivity that are simultaneously monitored in real-time within a dark-field microscopy setup. The approach allows for the statistical analysis of single-molecule interactions without requiring any labeling of the analyte. We study an antibody-antigen interaction (anti-biotin binding to biotin coupled to nanorods) and find that the waiting-time distribution is concentration-dependent and obeys Poisson statistics. The ability to probe hundreds of nanoparticles simultaneously will provide a sensor with a dynamic range of 7 decades in concentration and will enable the study of heterogeneity in molecular interactions.

Single-molecule detection has distinct advantages over ensemble-averaged techniques because it yields statistical distributions of molecular properties instead of averages, and reveals rare and unsynchronized events. Preferred embodiments of the invention include techniques for monitoring hundreds of single-molecule plasmonic sensors in real-time using total-internal-reflection excitation in a standard microscope. The waiting-time distribution of an antibody-antigen interaction obeys Poisson statistics and is concentration dependent. The parallelized detection provides a dynamic range of 7 decades in concentration.

In one implementation of the embodiments shown in FIGS. 6A-B, the superluminescent diode is a Superlum, with center wavelength 795 nm, bandwidth 14 nm, maximum power 35 mW. The detector 614 is a charge coupled device (CCD), e.g., with an area of 50×50 µm² on the sample surface.

The density of particles on the substrate may be controlled by the concentration during spin coating to yield 150-250 particles in a 100×100 µm² field-of-view of the microscope. Each particle site exhibits a different scattered intensity caused by (a) the inevitable dispersion in particle volume and aspect ratio leading to a different scattering cross-section at the irradiation wavelength, and (b) a different orientation of each particle in the partly polarized evanescent field. To ensure that the technique probes single nanorods, white-light scattering spectra of all the particles are recorded. Less than 10% of the particles are in clusters, which are discarded in the analysis.

The use of a superluminescent diode (SLD) as the light-source is important to achieve sufficient signal-to-noise ratio (S/N). The poor spatial coherence of light from an incandescent lamp provided insufficient intensity to image the small particles, whereas the high temporal coherence of laser illumination resulted in interference artifacts that induce signal fluctuations. SLD's are semiconductor high-gain devices that generate amplified spontaneous emission. In this application the low temporal coherence of the SLD significantly reduced interference artifacts whereas the high spatial coherence ensured a high illumination intensity. This resulted in shot-noise limited signals for an integration time of 100 ms.

In a typical single-molecule experiment an analyte is passed into the flow cell using a syringe pump. The CCD camera is used to record the time-dependent scattered signal (determined by a two-dimensional Gaussian fit of each spot in each frame). Plasmon shifts caused by biomolecular binding are then observed as step-wise changes in the normalized scattered intensity as a function of time using a step finding algorithm. Stepwise changes in the signal indicate stochastic binding of single antibodies (antibody concentration 10 nM). The sign of the stepwise changes depends on the plasmon wavelength relative to the wavelength of the irradiation source. The magnitude of the steps varies from 1% to 5%, with the variation of step-sizes indicating differences of position and orientation. The sign of the signal caused by analyte binding depends on the plasmon wavelength relative to the SLD wavelength. For particles with a plasmon wavelength shorter than the SLD wavelength the red-shift of the plasmon causes an increase in the scattered signal, whereas particles with a plasmon wavelength longer than the SLD wavelength exhibit the opposite behavior. A fraction of the particles does not exhibit step-wise changes of the signal because the plasmon wavelength is close to the SLD wavelength. For that reason the analysis may exclude particles with a plasmon resonance between 775 nm and 815 nm. It may also exclude steps with a S/N<2 (defined as the ratio between step-size and standard-deviation of the signal before analyte injection) which we attribute to drift of the background or analytes binding to the glass surface close to the particles.

Figure 7:
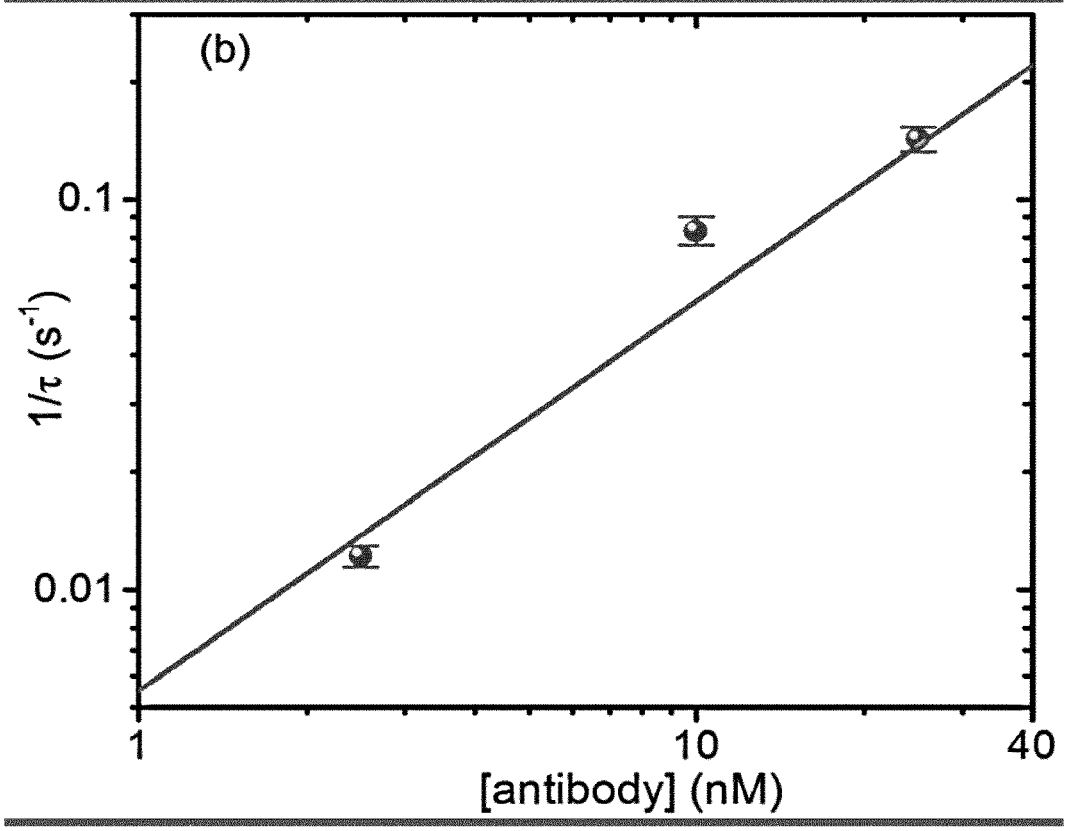
FIG. 7. is a graph or the mean binding rate lit vs. analyte concentration according to an embodiment of the invention.

From the step finding fit to the data the processor can estimate a value for the mean waiting-time $\tau$ between steps. The distribution of waiting-times obeys Poisson statistics, with a mean binding rate $1/\tau$ that depends on the analyte concentration according to a power law, as shown in the graph of FIG. 7.

Figure 8A:
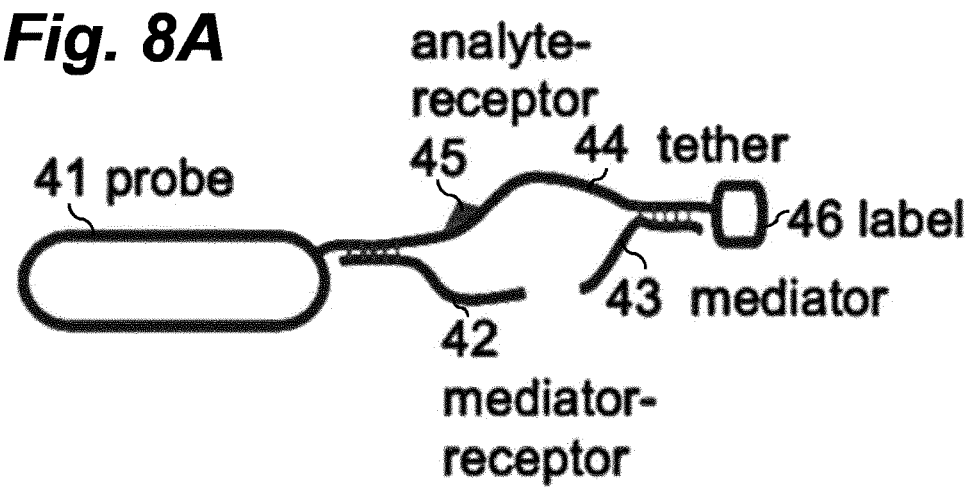
FIGS. 8A-B illustrate two configurations of a biosensing technique using a tethered mediator, according to an embodiment of the invention.
Figure 8B:

FIGS. 8A-B illustrate two configurations of an embodiment of a biosensor with tethered mediator. This embodiment is based on the same principle of operation as the embodiment of FIGS. 4A-D, but has a different underlying implementation. Biosensing probe 41 carries at least one mediator-receptor 42 on its surface. Mediator 43 is tethered to the probe via tether 44. The tether-mediator system contains at least one analyte-receptor 45, selected for binding to analyte. Label 46 enhances the signal measured by probe 41. FIG. 8A shows an open state, i.e., mediator-receptor and mediator are not bound. FIG. 8B shows a closed state, i.e., mediator-receptor and mediator are bound. The staircase bonds sketch the binding between series of nucleotides.

The distance and/or orientation between mediator-receptor and mediator can be measured in various ways. For example, probe 41 can be a plasmonic particle of which the plasmon resonance changes in dependence on the proximity and/or orientation of the mediator 43 and label 46 to the probe 41. For example, if the mediator or the label is non-spherical and has a long axis, then a change of orientation can give a change of plasmon resonance, even when the center of mass remains at the same position. Alternatively, tethered particle motion can be used as a detection method, e.g., probe 41 can be a substrate and label 46 can be a particle, of which the motion in the vicinity of the substrate depends on the binding between mediator and mediator-receptor. The particle will have a larger motion when mediator and mediator-receptor are not bound, and vice versa, the particle will have a smaller motion when mediator and mediator-receptor are bound. The position and motion of the particle can be recorded by optical methods, e.g., by the optically localizing the particle by its scattering characteristics. Changes of position, motion or motion patterns are indicative of association and/or dissociation events between mediators and mediator-receptor. A characteristic of association and/or dissociation events depends on whether the analyte is bound to the analyte-receptor, e.g., the frequency or duration of association or dissociation events, so that the presence of analyte can be determined.

The detected scattered intensity is obtained by fitting a particle's diffraction-limited spot in each frame with a two-dimensional Gaussian. The S/N (defined as the ratio between the mean and the standard-deviation of the signal over 150 seconds) increases for brighter particles. The S/N approaches the shot noise limit with some excess noise that is likely caused by fluctuations of the SLD intensity and slight mechanical drift of the sample. From these measurements we conclude that step-wise signal-changes of 1% can be detected with a S/N of 3-5 for particles with an integrated intensity over $10^5$ cnts/s.

The precision with which an analyte concentration can be determined is limited by counting statistics. For example, at least 100 molecules need to be detected in a defined time window in order to have a precision of concentration-determination of about $1/\sqrt{100}=10\%$. Small particles have a limited number of receptor molecules on their surface, so an individual particle can capture only a limited number of analyte molecules. Furthermore, in the limit of very low analyte concentration, there is a high probability that a single particle will not have captured even a single analyte molecule, even for long incubation times. To address this issue, a biosensing system according to preferred embodiments of the invention have at least 100 sensor particles, and time traces are recorded on the individual particles. The data of the particles is combined by the processor in order to determine an analyte concentration. For low analyte concentration, preferably data is combined from at least 1000 particles, more preferably at least 10,000 particles.

Due to variations during the fabrication process of the nanoparticles, they may have variable distinct sizes, resulting in inconsistent spectral properties. To address this issue, it is preferable to use particles with an inherently narrow distribution of plasmon resonances, e.g., gold bipyramids. The inventors have found that the ensemble line-width of the extinction spectrum of a solution of bipyramids approaches the single-particle line width of 50 nm, whereas the ensemble line width of gold nanorods is typically ~200 nm. This indicates that the individual bipyramids are optically more homogeneous. To address this issue it is also preferable to use a biosensing system with multiple wavelengths. A preferred solution is to record time-traces at a number of different wavelengths, e.g., using a wavelength-tunable superluminescent diode.

It is advantageous to have a biosensing system with a high number of particles. However, in a miniaturized system only a limited surface area is available. Furthermore, the density of particles on the surface is limited, because the optical system needs to be able to record time traces of individual objects. To address this issue, it is preferable to have system in which more than a predetermined fraction of the particles are separated from nearest-neighbor particles by at least the diffraction limit of the optical system. Another way to address this issue is to use an ordered pattern of particles on the surface, rather than a random distribution. Preferably the pattern of particles on the surface is conformal to the pattern of pixels on a digital camera chip. Digital cameras typically have rectangular pixels; for a camera chip with rectangular pixels, the particles are preferably situated on a rectangular grid. Another way to address this issue is to use an optical system in which a single particle maps onto a single pixel of a digital camera chip.

Preferably, a single particle gives a signal on a single pixel that is at least 5 times higher than the signal on that pixel caused by neighbouring particles. Another way to address this issue is to use particles with different spectral properties, patterned in an alternating way on a surface, with a minimal spacing below the diffraction limit. Due to the different spectral properties, sub-populations of particles can be selected and time-traces can be recorded on different sub-populations with single-particle resolution, even if they are spaced by less than the diffraction length.

In a particle-based biosensing technology with optical detection and single-particle resolution, it is important to identify and ignore undesired particle-like objects that are sources of noise. Particle-like objects of this kind may be related to sample contamination or aggregates in the sample, or because of biochemical properties of sensing particles (e.g., surface functionalization), particle properties (e.g., shape, optical properties), or configurations of particles with other particles (e.g., multi-particle aggregate, or multiple particles in proximity that cannot be optically resolved). To address this issue, spectral properties of these particles can be recorded and compared to reference data. The spectral properties can be recorded, e.g., using a broadband light source and tunable filter, or using a source with tunable wavelength. Spectral signals can be used to identify unreliable objects caused e.g., by particle properties (e.g., shape) or particle configuration (e.g., clusters of particles). Individual nanorods are characterized by a single narrow Lorentzian spectrum, allowing us to discard clusters based on the line shape and line width of the spectrum. Also, the scattering spectrum of clusters of nanoparticles exhibit a double peak or no clear peak at all. These clusters can easily be distinguished from the spectra of individual particles and are discarded from the data analysis.

Another technique to address this issue is to compare signal time-traces of individual objects with time-traces of a plurality of other objects. Objects having characteristics that strongly deviate from a plurality of other objects may be rejected, e.g., based on noise characteristics, drift, step sizes, number of steps, cumulative signal over a long time, etc.

The dynamic range of the sensor has low- and high concentration limits. Low analyte concentrations limit the statistics because the binding rate is low. For low concentrations, the minimum accessible concentration is determined by the number of particles in a field-of-view.

The 2D Gaussian fitting algorithm currently requires a region-of-interest of 10×10 pixels to obtain an accurate fit for a magnification of 60×. High-end scientific cameras having a resolution of over 5 megapixels have an estimated number of particles of 50 in a field-of-view under optimum conditions. The lowest accessible concentration is then about 0.5 pM. Higher analyte concentrations exhibit an increased rate of binding, for which a higher frame rate (i.e., a shorter integration time) is required to resolve all single-molecule binding events. Based on the Poisson distributed waiting times, a frame rate of 50/□ will ensure that the short times in the distribution are also resolved. By increasing the incident intensity from 64 W/cm$^2$ to 1 kW/cm$^2$ the integration time is reduced to 6 ms with only a modest reduction in S/N. The maximum frame rate that can be achieved is fundamentally limited by the photo-thermal heating of the nanoparticles. For studies on biological samples the maximum permissible temperature rise is of the order of 10 K, which we estimate is reached for an incident intensity of 10 kW/m$^2$. This implies that a frame rate of 20 fps is achievable without inducing thermal damage to the analyte. Such high frame rates give access to low-affinity interactions or to analyte concentrations as high as about 5 µM.

Probes for biosensing with single-molecule resolution (e.g., a metal nanoparticle, a dielectric resonator, a solid-state nanopore) typically exhibit a limited dynamic range due to the low number of binding sites per probe, prohibiting the accumulation of sufficient statistics at low analyte concentrations. This limitation is overcome in embodiments of the present invention by the parallelized probing of many sensors, giving an extraordinary projected dynamic range of 7 decades in concentration. The ability to extract distributions of molecular interaction parameters enables the investigation of heterogeneity in a population of unlabeled molecules. The simple and cheap optical layout allows the sensor to be implemented easily with a microscope.

High analyte concentrations will give binding events with a high rate of binding. This makes it complicated to resolve individual binding events in measured time-traces. Also, low-affinity interactions can give rise to short-lived states which are difficult to resolve. To address this issue, it is preferable to use an optical system with a high frame rate. Preferably the frame rate or reciprocal integration time is higher than 100 s$^{-1}$, more preferably higher than 1000 s$^{-1}$.

The temperature of the particles is crucial because the structure and activity of the tether protein can be impaired when it is heated for extended periods of time. Most globular proteins exhibit a melting temperature ranging from 40° C. to 80° C. depending on pH and buffer conditions. Based on a theoretical model, it is estimated that an incident intensity exceeding 10 kWcm$^{-2}$ is needed to raise the particle temperature by more than 10 K.

A high signal-to-noise ratio and high frame rate can be achieved using a light source with high power. However, a high optical power can give an unacceptable temperature rise in the sample fluid, thereby affecting the biochemical materials. To monitor this issue, an optical thermometer may be integrated with the system. For example, using a phase-sensitive camera, or monitoring the blue-shifted emission from the metallic particles, may be implemented. To maintain an acceptable temperature the incident power can be adjusted.

A drift of optical signal from the particles due to binding and unbinding events complicates the observation of signals. To address this issue, it is preferable to use an internal reference to continuously or periodically calibrate the optical signal, e.g., a particle or another fiducial object with optical activity on the surface, which gives a stable optical scattering signal, without resonant properties and without sensitivity to molecular binding. The signal from a reference particle will be an optical reference for the illumination and detection status of the system. The reference signal can be used by the processor to correct for fluctuations in the optical signals from the biosensing particles, caused by drift in the components of the optical system and fluctuations of the intensity of the light source. The use of multiple reference particles on the surface will further improve the calibration. Examples of reference or fiducial markers are polystyrene spheres, nanopatterned surface structures, PDMS islands. Optical signal fluctuations can be caused by changes of optical path length, e.g., perpendicular to the imaging plane (z-axis). To address this issue, it is preferable to have an active z-axis feedback and control in the system.

Analyte multiplexing, i.e., measurement of different analytes at the same time, is advantageous for increased biomedical sensitivity and specificity. To provide for such multiplexing, some embodiments use particles that have different receptors on their surface. For reasons of counting statistics and precision, the number of particles should be at least equal to 100 for every analyte, and higher when necessary for an analyte with a low binding event rate (e.g., because it has a low concentration, or due to the affinity and density of the receptors). The minimal frame rate of the optical system is determined by the analyte with the highest (un)binding event rate. Also, some embodiments use particles with different optical properties, so that the different particles can be mixed. The particles preferably have at least two sub-populations that can be optically distinguished and that have different receptors on their surface. Also in this case, for reasons of counting statistics and precision, the number of particles is preferably at least 100 for every analyte, and higher for an analyte with a low binding event rate (e.g., because it has a low concentration, or due to the affinity and density of the receptors). The minimal frame rate of the optical system is determined by the analyte with the highest event rate.

Monitoring the multimer distribution in a sample (e.g., monomer versus dimer, trimer, tetramer) is important in biotechnology, e.g., in the development and production of biopharmaceuticals.

Solution:

Identify the state (monomer, dimer, trimer, etc.) within detection events. The multimer distribution may be derived from step statistics, e.g., when the step signal depends on the mass of the bound analyte. E.g., in case of detection using plasmonic nanorods, the size of the plasmon change depends on the mass of the bound analyte. Higher order aggregates of analyte (dimer, trimer, etc.) have a higher mass and could then be distinguished by analysing the size of the signal and/or by the time characteristics of the signal. When (un)binding is recorded with single-molecule resolution, then a histogram of molecular masses can be established.

The features described in various separate embodiments of the invention are not necessarily exclusive and, in general, may be used in combination with each other. Such features and embodiments also include material disclosed in U.S. provisional patent applications 62/078,870 filed Nov. 12, 2014, 62/092,763 filed Dec. 16, 2014, 62/132,096 filed Mar. 12, 2015, and 62/159,235 filed May 9, 2015, all of which are incorporated herein by reference.

The invention claimed is:

1. A method for sensing an analyte, the method comprising:
    bringing a matrix containing the analyte into contact with a sensor device having a multitude of biosensor probes attached to a surface of the sensor device, wherein the biosensor probes comprise detection probes conjugated to mediator-receptors that are not binders for the analyte;
    providing in the sensor device mediators conjugated to analyte-receptors, where the mediators are selected to bind to the mediator-receptors, and where the analyte-receptors are selected to bind to the analyte, wherein the mediators are bound to the detection probes by tether molecules, or tether molecule fragments, or tether domains;
    detecting by an optical or electrical sensor changes over time of distance and/or relative orientation between the mediators and the mediator-receptors, indicative of a sequence of single-molecule association and/or dissociation events between the mediators and the mediator-receptors over time;
    wherein a change in a characteristic of the sequence of single-molecule association and/or dissociation events indicates whether the analyte is bound to the analyte-receptors
    and
    determining a presence of the analyte by detecting the change in the characteristic of the sequence while the matrix is in contact with the sensor device.

2. The method of claim 1 wherein the matrix is a fluid or analyte-permeable matrix.

3. The method of claim 1 wherein determining the presence of the analyte comprises performing histogram and/or histogram processing to establish a histogram of molecular masses.

4. A sensor device for sensing an analyte located in a matrix, the sensor device comprising:
    (a) a multitude of biosensor probes attached to a surface of the sensor device, wherein the biosensor probes comprise detection probes conjugated to mediator-receptors that are not binders for the analyte;
    (b) analyte-receptors selected to bind to the analyte;
    (c) mediators conjugated to the analyte-receptors, where the mediators are selected to bind to the mediator-receptors; wherein the mediators are bound to the detection probes by tether molecules, or tether molecule fragments, or tether domains; and
    (d) an optical or electrical sensor configured to detect changes over time of distance and/or relative orientation between the mediators and the mediator-receptors, indicative of a sequence of single-molecule association and/or dissociation events between the mediators and the mediator-receptors;

wherein a change in a characteristic of the sequence of single-molecule association and/or dissociation events indicates whether the analyte is bound to the analyte-receptors, and wherein the optical or electrical sensor is configured to determine a presence of the analyte from the change in the characteristic of the sequence while the matrix is in contact with the sensor device.

5. The sensor device of claim 4 wherein the optical or electrical sensor comprises a lens and an imaging detector.

6. The sensor device of claim 4 further comprising a superluminescent diode (SLD) and a lens configured to generate and direct excitation light at the biosensor probes.

* * * * *